(12) United States Patent
Braun et al.

(10) Patent No.: US 6,890,900 B2
(45) Date of Patent: May 10, 2005

(54) METHODS FOR TREATING OR PREVENTING DISEASES OF THE ORAL CAVITY

(75) Inventors: Steven D. Braun, Oneonta, NY (US); Ram Nimmagudda, Oneonta, NY (US)

(73) Assignee: Campina B.V., Zaltbommel (NL)

( * ) Notice: Subject to any disclaimer, the term of this patent is extended or adjusted under 35 U.S.C. 154(b) by 0 days.

(21) Appl. No.: 10/263,723

(22) Filed: Oct. 4, 2002

(65) Prior Publication Data

US 2003/0114364 A1 Jun. 19, 2003

Related U.S. Application Data

(63) Continuation of application No. 09/854,930, filed on May 15, 2001, now Pat. No. 6,482,396.

(51) Int. Cl.[7] .......................... A01N 37/18; A61K 38/16
(52) U.S. Cl. ................................. 514/8; 514/2
(58) Field of Search ........................ 514/2, 8; 424/50, 424/49, 406

(56) References Cited

U.S. PATENT DOCUMENTS

| | | |
|---|---|---|
| 4,157,386 A | 6/1979 | La Rochelle |
| 4,363,820 A | 12/1982 | Ernster |
| 4,545,933 A | 10/1985 | Ernster |
| 4,762,822 A | 8/1988 | Ettinger |
| 4,816,398 A | 3/1989 | Brule et al. |
| 4,902,681 A | 2/1990 | Schreiber |
| 4,992,420 A | 2/1991 | Neeser |
| 4,994,441 A | 2/1991 | Neeser |
| 5,063,203 A | 11/1991 | Drouet et al. |
| 5,075,424 A | 12/1991 | Tanimoto et al. |
| 5,147,853 A | 9/1992 | Dosako et al. |
| 5,260,280 A | 11/1993 | Isoda et al. |
| 5,262,151 A | 11/1993 | Montgomery |
| 5,270,033 A | 12/1993 | Montgomery |
| 5,270,351 A | 12/1993 | Bowen |
| 5,296,464 A | 3/1994 | Tomita et al. |
| 5,330,975 A * | 7/1994 | Isoda et al. |
| 5,344,820 A | 9/1994 | Dosako et al. |
| 5,424,396 A | 6/1995 | Tomita et al. |
| 5,538,714 A | 7/1996 | Pink et al. |
| 5,576,299 A * | 11/1996 | Ando et al. |
| 5,607,681 A | 3/1997 | Galley et al. |
| 5,624,906 A | 4/1997 | Vermeer |
| 5,629,282 A | 5/1997 | Bhakoo |
| 5,670,138 A | 9/1997 | Venema et al. |
| 5,688,492 A | 11/1997 | Galley et al. |
| 5,739,177 A | 4/1998 | Ohno et al. |
| 5,741,773 A * | 4/1998 | Zhang et al. |
| 5,756,559 A | 5/1998 | Blackwell et al. |
| 5,798,336 A | 8/1998 | Travis et al. |
| 5,830,489 A | 11/1998 | Valenti et al. |
| 5,834,424 A | 11/1998 | Valenti et al. |
| 5,843,471 A | 12/1998 | Chaykin |
| 5,853,704 A | 12/1998 | Zhang et al. |
| 5,866,629 A | 2/1999 | Santerre et al. |

OTHER PUBLICATIONS

Kawasaki et al, "Inhibition by Lactoferrin and κ–Casein Glycomacropeptide of binding of *cholera* Toxin to its Receptor", Biosci. Biotech. Biochem. 56(2):195–198 (1992).

Ohtani and Yamada, "Characterization of bovine colostral proteins wih inhibitory activity in passive cutaneous anaphylaxis", Milchwissenschaft 49(1):20–24 (1994).

Xu et al, "In vitro susceptibilty of *candida* species to lactoferrin", Medical Mycology 37:35–41 (1998).

Yamada et al, "Stimulation and Inhibition of Interferon–β Production of Human Diploid Fibroblasts by Foodstuffs", Agric. Biol. Chem. 55(3):829–832 (1991).

Neeser et al, "Specific and Nonspecific Inhibition of Adhesion of Oral Actinomyces and Streptococci to Erythocytes and Polystyrene by CaseinoGlycopeptide Derivatives", Infection and Immunity 56(12):3201–3208 (1988).

Smithers et al, Symposium: Advances iin Dairy Foods Processing and Engineering, "New Opportunities from the Isolation and Utilization of Whey Proteins", J. Dairy Sci. 79:1454–1459 (1996).

Tenovuo et al, "Salivary lysozyme, lactoferrin and peroxidases: antibacterial effects on cariogenic bacteria and clinical applications in preventive dentistry", Proc Finn Dent Soc 87(2):197–208 (1991).

Soukka et al, "Agglutination of *Streptococcus Mutans* Serotype C Cells but Inhibition of *Porphyromonas Gingivalis* Autoaggregation by Human Lactoferrin", Archs Oral Biol. 38(3):227–232 (1993).

Kussendrager, "Lactoferrin and Lactoperoxydase", IFI 6:17–21 (1993).

Kawasaki et al, "Inhibition by κ–Casein Glycomacropeptide and Lactoferrin of Influenza Virus Hemagglutination", Biosci. Biotech. Biochem. 57(7):1214–1215 (1993).

Custer, Mary Cathe, "Partial Characterization of an Inhibitor of Bacterial Spore Outgrowth That is Thermally Derived From Nitrite and the Formation of Analogous Inhibi", Dissertation, Degree Date (1983), UMI Dissertation Services A Bell & Howell Company, Ann Arbor, Michigan.

* cited by examiner

*Primary Examiner*—Patricia Leith
*Assistant Examiner*—Randall Winston
(74) *Attorney, Agent, or Firm*—Nixon & Vanderhye P.C.

(57) ABSTRACT

The present invention relates to a method of reducing dental plaque and calculus deposition. The invention further relates to a method of treating or preventing periodonitis and other diseases of the teeth and tissues of the oral cavity. The invention further relates to compositions suitable for use in such methods.

8 Claims, 6 Drawing Sheets

METHODS FOR TREATING OR PREVENTING DISEASES OF THE ORAL CAVITY

This application is a continuation of application Ser. No. 09/854,930, filed May 15, 2001, now U.S. Pat. No. 6,482,396, the entire content of which is hereby incorporated by reference in this application.

TECHNICAL FIELD

The present invention relates to a method of reducing dental plaque and calculus deposition. The invention further relates to a method of treating or preventing periodonitis and other diseases of the teeth and tissues of the oral cavity. The invention also relates to compositions suitable for use in such methods.

BACKGROUND

A crucial function of human saliva is to protect oral tissues from the destructive effects of microorganisms. Since the oral cavity is a major route of entry for foreign and sometimes harmful bacteria into the body, it is necessary to keep a balanced, healthy flora. The balance between bacterial aggregation, stimulation, and prevention of adherence and growth, partially determines the development and composition of the oral microbiota. Certain normal oral flora bacteria have pathogenic potential if their population growth exceeds the normal oral flora balance.

Dental plaque, which develops on tooth enamel, can cause inflammation of gingival tissues giving rise to gingivitis. Chronic gingivitis is associated with the accumulation at the gingival margin of suptagingival dental plaque. There is a shift in the microbial composition of plaque in gingivitis away from a streptococci-dominated flora towards higher levels of pathogenic species. Over time, gingival inflammation and constant exposure to pathogenic oral bacteria can cause periodontitis. This most severe form of oral infection causes deterioration of tooth supporting tissues.

Lactoferrin (LF) is an iron-binding glycoprotein found in several mammalian exocrine secretions, such as milk and saliva. LF binds two atoms of $Fe^{3+}$ and thus limits the availability of this essential nutrient for bacteria thereby causing an indirect bacteriostatic effect (Cole et al, Microbial aspects of dental curies, pp. 359–373, Information Retrieval, Washington, D.C. 1976). The iron-free form of LF damages the outer membrane of gram-negative bacteria by altering membrane function and permeability. LF also contains sialic acid. Human and bovine milk, which have sialic acid-containing fragments of k-casein, exert an antibacterial effect by binding LF to the bacterial cell wall and inhibiting the microbial adhesion to surfaces.

Glycomacropeptide (GMP), or k-casein glycomacropeptide, is a peptide prepared by food grade enzymatic hydrolysis and fractionation. The powder usually contains 89% GMP protein. The product contains glycosylated GMP (N-acetylneuraminic acid commonly known as sialic acid) and non-glycosylated GMP. It is the sugar chains containing sialic acid that are crucial for binding to bacteria surfaces (Kawasaki, Biosci. Biotech. Biochem. 56:195–198 (1992)). Since these chains bind to the active sites on certain oral bacteria, GMP acts to inhibit bacterial growth by binding to them, thereby keeping growth phase numbers from increasing (Kawasaki, Biosci. Biotech. Biochem. 57:1214–1215 (1993)).

The present invention results from studies designed to assess the efficacy of LF and GMP as anti-microbial agents. The bacteria tested in these studies include Streptococcus mutans, Streptococcus pyogenes, Actinobacillus haemophilus, and Pseudomonas aeruginosa. S. mutans is an alpha-hemolytic (partial destruction of red blood cells (RBCs) and hemoglobin that produces a greenish discoloration of the blood agar plate), nonmotile, facultatively anaerobic, Gram-positive cocci. The oral streptococcus species is found in the mouth cavity and upper respiratory tract of humans. These organisms hydrolyze sucrose and form dental plaque, and, as a result, create an anaerobic environment ideal for fermentation. S. pyogenes is a beta-hemolytic (complete destruction of RBCs and hemoglobin and result in a clearing around the growth on a blood agar plate) nonmotile, encapsulated, facultatively anaerobic, Gram-positive cocci. This species is responsible for strep throat, impetigo, middle ear infections, mastoiditis, and an array of infections resulting from hematogenic dissemination of the organism. It resides in the nose, throat and skin and when it becomes attached to host cells, it releases toxins that cause inflammation. P. aeritginosa is an aerobic, highly motile, straight or slightly curved, Gram-negative rod. It is common in soil and water and finds its way into the host by digestion, inhalation or through openings in the skin. It secretes tissue-damaging enzymes and forms a biofilm on dentures causing oral infections in denture users. A. haemophilus is an anaerobic, nonmotile Gram-positive cocci bacterium that is the most commonly found pathogen in individuals that have certain forms of periodontal disease. It leads to swelling of the gum tissue and the formation of periodontal pockets. It is less likely to be found in healthy oral flora.

Although S. mutens, S. pyogenes, A. haemophilus and P. aeruginosa are widely distributed among humans, an increased number in oral flora causes sore throats, scarlet fever, dental caries, gingivitis, and periodontitis. When populations of these bacteria exceed the normal flora amount, they begin to denature proteins, killing host leukocytes, host molecules, and dissolving blood clots. The goal of the studies that resulted in the present invention was to determine whether specific concentration levels could be identified at which LF and GMP would act as natural anti-microbial agents for the maintenance of oral flora.

SUMMARY OF THE INVENTION

The present invention relates to a method of reducing dental plaque and calculus deposition. The invention further relates to a method of treating or preventing periodonitis and other diseases of the teeth and tissues of the oral cavity. The invention further relates to compositions suitable for use in such methods.

Objects and advantages of the present invention will be clear from the description that follows.

DETAILED DESCRIPTION OF THE INVENTION

Figure 1:
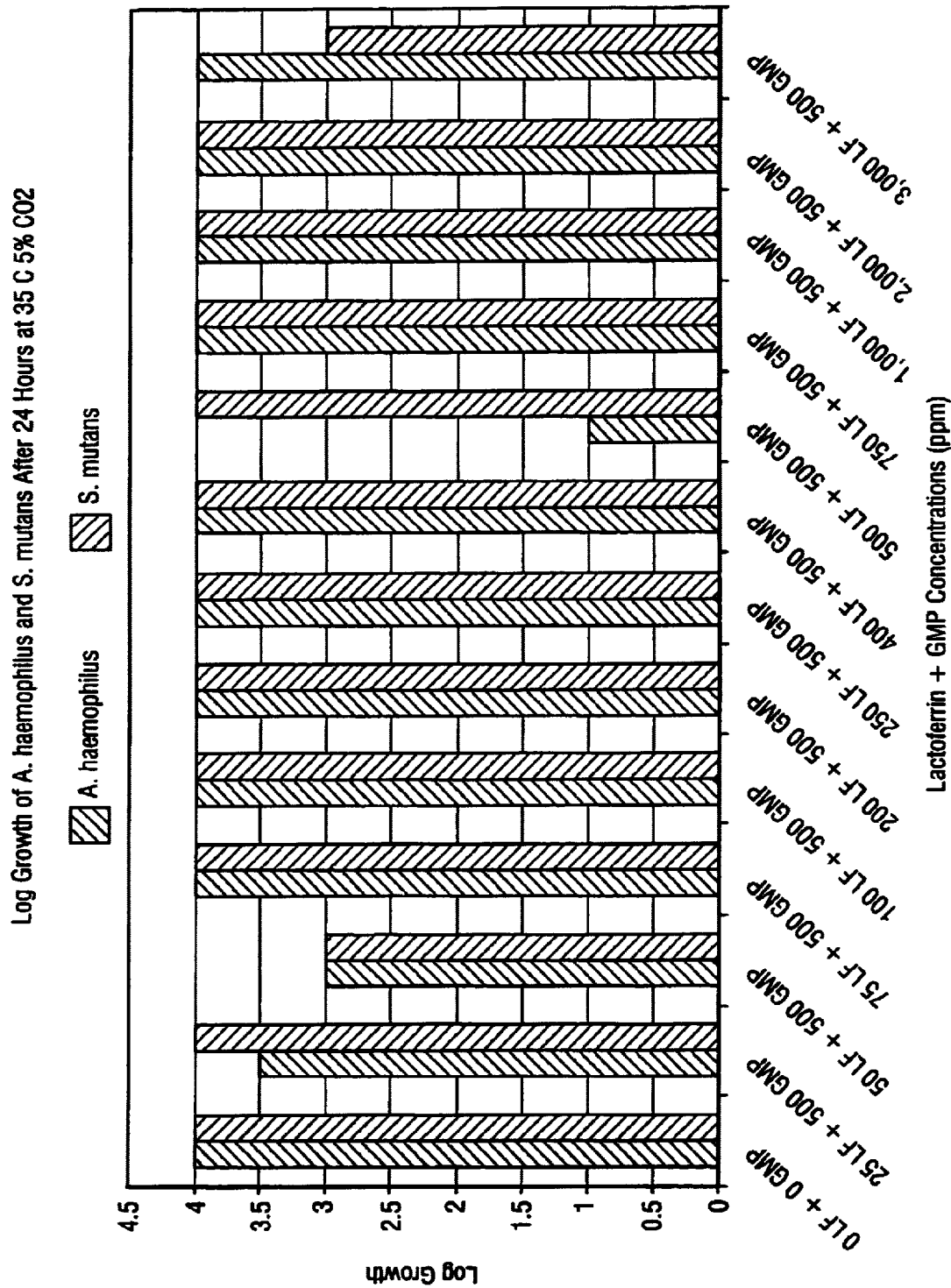
FIG. 1 shows log growth of A. haemophilus and S. mutans after 24 hours at 35° C., 5% $CO_2$, in the presence of varying concentrations of LF and a fixed concentration of GMP.

The present invention is based on the observation that LF and GMP exert an anti-microbial effect against, for example, *A. haemophilis* when used in specific combinations. Studies from which the invention results demonstrate that 500 ppm/500 ppm formulations of LF/GMP are surprisingly effective against *A. haemophilis*.

The present invention relates to a method of inhibiting dental plaque formation and calculus deposition. The invention also relates to a method of treating or preventing periodonitis and as well as other diseases of the teeth and tissues of the oral cavity. Further, the invention relates to oral hygiene compositions comprising LF and GMP suitable for use in such methods.

In the oral hygiene composition of the invention, the mixture of LF and GMP (advantageously, 500 ppm/500 ppm LF/GMP in the case of *A. haemophilus*) can be formulated with a substantially non-toxic carrier (that is, a carrier suitable for use in the oral cavity of a mammal, particularly, a human). The product can take the form of a mouthwash, mouth rinse, tooth powder, toothpaste or tooth gel, chewing gum, or other dentifrice that can be readily removed from the mouth and discarded after use. Ingredients, other than LF and GMP, typically found in mouth washes and rinses, tooth powders, pastes and gels, and chewing gums, can be used in the preparation of the composition of the invention and routine preparative methodologies can be employed (see, for example, U.S. Pat. No. 5,362,480).

LF and GMP are present in the instant composition in amounts sufficient to inhibit the growth of, for example, *A. haemophilis*. Optimum amounts of LF and GMP can vary, for example, depending on the microorganism to be growth inhibited, the form of the composition (e.g., chewing gum versus mouthwash), and other factors. Optimum concentrations of LF and GMP and/or ratios of LF to GMP can be established readily by one skilled in the art, for example, using assays described in the Example that follows.

The composition of the invention can be used at any time, however, use shortly after meals, or after consumption of beverages or snacks, can be particularly advantageous. The length of time of use can be at the individual's convenience and as typical for the form taken by the composition.

While the invention is directed at human use, it will be appreciated that veterinary use is also contemplated. Obviously, acceptable forms of the composition may be more restricted when use in non-human animals is involved.

As indicated above, inhibition of development of dental plaque and calculus is a principle focus of the invention. It will be appreciated, however, that a variety of oral lesions are susceptible to treatment or prevention in accordance with the invention, including gingival disease. Compositions suitable for use in connection with these lesions can be formulated and used as described above.

Certain aspects of the present invention are described in greater detail in the non-limiting Examples that follow. Present studies clearly demonstrate that both LF and GMP create a specific interaction between the tested bacteria (*A. haemophilus, S. mutans, S. pyogenes, P. aeruginosa*, and oral flora). This interaction causes an anti-microbial effect because bacteria populations decrease in the presence of LF and GMP and increase without them. Earlier studies found that the terminal carbohydrate sequence containing sialic acids plays a role in inhibitory activities. There was not one concentration that worked on all the tested bacteria. Therefore, it is not only the structure of the sialic acid sequences that is important but also other factors, such as a variety of carbohydrate groups, the three-dimensional protein structure, acid conditions (low pH), and the availability of the active binding site on each of the different strains of bacterium. Although sialic acid appears to be the driving force in LF's and GMP's effectiveness, sialic acid by itself does not inhibit the growth of bacteria. Therefore, there are components present in these proteins (LF and GMP) that have a synergistic effect on microbial binding and growth inhibition. When the MIBC of LF and GMP are combined and do not work, they may be counter-acting each other. Since LF is significantly larger (80,000 Da) than GMP (9,000 Da), LF may be interfering with GMP's binding to microorganisms. Bacteria, showing a maximum reduction of one tog (*S. mutans, S. pyogenes*, and oral flora), are more resistant to LF and GMNP. There are less specific interactions between LF and GMP and the outer membrane proteins of these bacteria, making binding more difficult. With respect to differences, a change in temperature may also play a role in the efficiency of LF and GMP which may have varying effects on bacteria under different conditions. Different amounts of LF and GMP may be needed for different growth phases of the bacteria. For example, at higher temperatures (35° C.), most bacteria grow much more rapidly. Therefore, greater mixed concentrations may be more effective.

EXAMPLE

Experimental Details

Bacterial strains used in this study were *Pseudomonas aeruginosa* ATCC #27853, *Streptococcus mutans* ATCC #33535, *Streptococcus pyogenes* ATCC #19615, and *Actinobacillus haemophilus* ATCC #43717 and an oral swab from a healthy adult. Bacteria were grown on blood/BHT media (Brain Heart Infusion Agar with protease peptone, sodium chloride, glucose, di-sodium phosphate, and agar, Oxoid, Hampshire England, Sheep's Blood) in the presence of 5% $CO_2$ at 35° C. Bacteria were harvested by swabbing inoculated growth plates after 24 hours and diluting the colonies in 9 ml of deionized water (DI water) until a suspension of 0.5 McFarland Turbidity Standard was reached using the nephelometer (McFarland Turbidity Meter). The 0.5 McFarland value is approximately equivalent to $1.0 \times 10^8$ organisms. One ml of the appropriate bacterial dilution was taken using a sterile pipette and introduced into 8 ml of sterilized BHI broth. (Preparation of BHI broth: 37 g+1,000 ml DI water, Difco Laboratories. By pipette, 9 ml of broth was placed into medium test tubes as means of a control and 8 ml test tubes were prepared for the concentration tests).

Bovine LF and GMP, purified from milk, were provided by DMV International Nutritionals Fraser, N.Y. Sodium bicarbonate enzyme grade was purchased from Fisher Scientific, N.J. Hydrochloric acid (HCl) used was at 0.1N. N-acetylneuraminic acid (sialic acid type VI) from *Escherichia coli* was purchased from Sigma Chemical Co., St. Louis Mo.

LF and GMP Assay

Both LF and GUT were diluted with sodium bicarbonate. In experiments where LF and GMP were used in combination, they were diluted with sodium bicarbonate. Sodium bicarbonate is a proven binding enhancer with LF. It creates more binding sites, making adhesion to microbial cells easier thus making LF and GMP more effective. A 0.10 mM concentration of sodium bicarbonate (molecular weight 84.1 g) was made and the pH was brought to 5.2–5.3 using 1N HCl. Preparation example of sodium bicarbonate (pH 4.23):

1- $\dfrac{84.1 \text{ g}}{1000 \text{ ml } DI \text{ water}} = 1$ M Solution

2- $\dfrac{0.1 \text{ ml of 1 M Solution}}{1000 \text{ ml } DI \text{ water}} = 0.1$ mM Sodium Biocarbonate 3- Adjust pH by adding 0.1 N HCl Sterilization techniques for sodium bicarbonate, LF, and GMP required filtration through a 0.45 μm filter. LF (DMV International)/GMP (DMV International) were dissolved in the sodium bicarbonate solution to form a 100,000 ppm LF/GMP "mother dilution". This solution was filtered through a 0.45 μm filter. Dilutions containing varying ppm's (0, 25, 50, 75, 100, 200, 250, 400, 500, 750, 1,000, 2,000 and 3,000 ppm) were made using the 100,000 ppm "mother dilution" and adding the sterilized 0.10 mM sodium bicarbonate into a sterile centrifuge tube. Example for calculating 2,500 ppm dilution (1,000 ppm=0.1%):

$V_1 C_1 = V_2 C_2$ $V_1 (100,000 \text{ ppm}) = (2,500 \text{ ppm})(1,000 \text{ ml})$ $V_1 = \dfrac{25 \text{ ml } LF/GMP \text{ "mother dilution"}}{975 \text{ ml } 0.1 \text{ mM sodium bicarbonate}} >$ Equal 1,000 ml To study the kinetics of LF/GMP binding, each strain of bacteria was taken separately with a sterile pipette and placed into an 8 ml BHI broth test tube, vortexed, and incubated in the presence of 1 ml of LF or GMP for 18–24 hours at 35° C. with 5% $CO_2$. In the combination procedure, 0.5 ml of both LF and GEP were taken as 1 ml inoculations.

Sialic Acid Assay

The glycosylated fraction of GMP contains sialic acid (NANA). Total NANA content expressed on GMP is typically 6.5%. Sialic acid was tested to determine if it was the driving force in microbial inhibition. Pure sialic acid (Lot #117H0802) was tested at 1,000 ppm:

1,000 ppm=0.1%

0.001 g=1,000 ppm $\dfrac{0.001 \text{ g Sialic Acid}}{1 \text{ g } QS \text{ Sodium Bicarbonate}} = \dfrac{0.1 \text{ g Sialic Acid}}{100 \text{ g } QS \text{ Sodium Bicarbonate}}$ One mL of each bacterial strain, plus one mL of sialic acid solution (1,000 ppm) were inoculated into test tubes filled with 8 mL of BHI broth. Each test tube was vortexed, incubated for 24 hours at 35° C. with 5% $CO_2$, and then pour plated in BHI agar to obtain a plate count.

Viable Plate Count

This technique was used to determine the density of living (viable) cells in inoculated broth cultures. It involves plating a bacterial sample and counting the resulting colonies after incubation. A serial dilution of the original broth was taken prior to plating. The serial dilution is necessary to reduce the density of organisms in order to create countable plates. Only plates containing between 25 and 250 colonies are considered countable. Cell densities are traditionally recorded as CFU (colony forming unit)/ml. By convention, when 1.0 ml is inoculated onto a plate, the dilution factor (DF) is recorded as tenfold greater. Formula:

Original cell density = $\dfrac{\#CFU}{(\text{Volume plated})(DF)}$

If 120 colonies are counted on a plate inoculated with 1.0 ml of solution having a DF of $10^{-5}$, the original density is as follows:

Original cell density=120 CFU/(1.0 ml) ($10^{-5}$)

Original cell density=$1.2 \times 10^7$ CFU/ml

The assays required the use of a pour plate technique. The pour plate technique adds a step to the conventional serial dilution. The 1 ml of dilution is added to a warm emulsion of dilute nutrient (BHI) agar to produce an agar overlay in the petri plates. After incubation, the bacterial growth covers the entire plate but individual cellular movement has been restricted by the soft agar overlay. Each colony formed is assumed to have originated from a single CFU. The plates were gently mixed, inverted, and incubated for 18–24 hour at 35° C.

Identifying Normal Oral Flora

There is a mixture of microorganisms obtained in "normal oral flora." Testing a swab taken from a healthy mouth cavity aided in the identification of the most common mouth flora. Experiments were conducted with the mouth culture to determine the antimicrobial effects of LF and GMP.

Oral cultures were grown on BHI agar with added sheep's blood for 24 hours at 35° C. 5% $CO_2$. The microorganisms were diluted by a factor of $10^{-6}$ and 1 mL of this dilution was pour plated in BHI agar. These plates were incubated for another 24 hours. Here, isolated colonies were taken and were streaked on a BHI/Blood plate for growth of a pure culture. Streaking a plate produces isolated growth of microbial species in a mixed culture sample. Once isolated, pure cultures can be tested for species identification. The isolated colonies were Gram-stained to distinguish between Gram-positive and Gram-negative cells. The Gram stain is a differential stain in which a decolorization step occurs between the application of two basic stains. The next step was a catalase test to identify the organisms that produce the enzyme catalase. It was used to differentiate members of the catalase-positive *Micrococcaceae* and *Staphylococci* from the catalase-negative Streptococcaceae. Hydrogen peroxide was added to the bacteria and observed for a reaction (evidence of bubbles being formed).

The last identification technique required the use of API 20 Strep kit (bioMérieux Vitek, Inc. Mo.). API 20 Strep is a standardized method combing 20 biochemical tests. It enables species identification of most Streptococci. Using an Analytical Profile Index, the pattern of the reactions were coded by number and identified by its final numerical profile.

In the oral culture, three isolated colonies were tested for identification from a swabbed mouth cavity. Gram staining revealed all colonies to be a Gram-positive cocci. The next step required the catalase test, which had a negative reaction. This negative-catalase reaction was a confirmation of a streptococcus species. The API 20 Strep test was done on all three pure cultures to identify each species. The numbers were the results of the API 20 test. The bacterial species was determined using the Analytical Profile Index. The numerical results were as follows:

Pure culture #1: 50-52-671=*Streptococcus salivaris*
Pure culture #2: 50-70-771=*Streptococcus salivaris*
Pure culture #3: 50-70-671=*Streptococcus salivaris*

Results

I. Identifying the MIBC for LF and GMP

A. Minimum Inhibitory Concentration (MIBC) of LF

Using a control (one broth tube inoculated with a bacterial strain, but no LF), the effectiveness of LF was examined. Each test tube containing a specified amount of LF (50, 100, 250, 500, 1,000 ppm and 3000 ppm) was diluted and plates were poured. After incubating the plates for 24 hours at 35° C. with 5% $CO_2$ (the normal conditions of an oral cavity), the bacterial recovery count was taken and the results were compared to the control. *A. haemophilus, S. mutans, S. pyrogenes* and an oral culture were tested at 35° C. *Pseudomonas aeruginosa* was tested at both room temperature and 35° C. with 5% $CO_2$. This was done because *P. aeruginosa* is not strictly an oral pathogen. It is commonly found in the environment in various conditions. It can be found in the environment and oral intake can cause inflammation in the oral cavity. Most normal oral bacteria are only found in the mouth and are not taken in from outside factors. Therefore, *P. aeruginosa* is a threat in both temperature settings. Table 1 depicts the minimum inhibitor concentration (MBEC) for each of the bacterial strains at 35° C. *S. pyogenes* and the oral culture were not effected by LF at any tested concentration. The other concentrations showed no log reduction because their numbers were close to the control when incubated for 24 hours at 35° C. (see Table 2).

TABLE 1

| Bacteria | MIBC of LF | |
|---|---|---|
| | LF ppm | # Log Reductions |
| *P. aeruginosa* (35° C.) | NCF | 0 |
| *A. haemophilus* (35° C.) | 3,000 | 1 |
| *S. mutans* (35° C.) | 3,000 | 1 |
| *S. pyogenes* (35° C.) | NCF | 0 |
| Oral (35° C.) | NCF | 0 |

*NCF = No Effective Concentration Found

TABLE 2

Colony Counts of LF

| Bacteria | Initial | 0 ppm | 50 ppm | 100 ppm | 250 ppm | 500 ppm | 1,000 ppm | 3,000 ppm |
|---|---|---|---|---|---|---|---|---|
| *A. haemophilus* (35° C.) | $6.2 \times 10^4$ | $2.7 \times 10^8$ | $2.6 \times 10^8$ | $2.5 \times 10^8$ | $2.5 \times 10^8$ | $2.3 \times 10^8$ | $2.4 \times 10^8$ | $5.3 \times 10^7$ |
| *S. mutans* (35° C.) | $9.6 \times 10^4$ | $1.8 \times 10^8$ | $1.9 \times 10^8$ | $1.9 \times 10^8$ | $1.7 \times 10^8$ | $1.4 \times 10^8$ | $1.2 \times 10^8$ | $5.5 \times 10^7$ |
| *S. pyogenes* (35° C.) | $8.6 \times 10^4$ | $6.2 \times 10^7$ | $5.8 \times 10^7$ | $1.5 \times 10^7$ | N/A | $7.8 \times 10^7$ | N/T | $1.7 \times 10^8$ |
| *P. aeruginosa* (35° C.) | $5.2 \times 10^4$ | $6.6 \times 10^8$ | $4.6 \times 10^8$ | $3.6 \times 10^8$ | $2.6 \times 10^8$ | $2.3 \times 108$ | $3.2 \times 10^8$ | $1.2 \times 10^8$ |
| Oral (35° C.) | $7.1 \times 10^3$ | $4.7 \times 10^8$ | $4.8 \times 10^8$ | $4.2 \times 10^8$ | $4.3 \times 10^8$ | $4.0 \times 10^8$ | $3.9 \times 10^8$ | $3.4 \times 10^8$ |

N/T—Not Tested

B. MIBC of GMP

Similar concentrations were made for GMP as were prepared for LF. *A. haemophilits* and *S. mutans* were affected by GMP at a much lower ppm level (500 ppm). *S. pyogenes* and the oral flora showed no growth change in the presence of GMP alone, therefore an effective concentration was not found (see Tables 3 and 4). *Pseudomonas* was tested at both 23° C. and 35° C. and neither showed a log reduction.

TABLE 3

| Bacteria | MIBC of GMP | |
|---|---|---|
| | GMP ppm | # Log Reductions |
| *S. mutans* (35° C.) | 500 | 1 |
| Oral (35° C.) | NCF | 0 |
| *P. aeruginosa* (35° C.) | NCF | 0 |
| *A. haemophilus* (35° C.) | 500 | 1 |
| *S. pyogenes* (35° C.) | NCF | 0 |

*NCF No Effective Concentration Found

TABLE 4

Colon Counts of GMP

| Bacteria | Initial | 0 ppm | 50 ppm | 100 ppm | 250 ppm | 500 ppm | 1,000 ppm | 3,000 ppm |
|---|---|---|---|---|---|---|---|---|
| A. haemophilus (35° C.) | $1.6 \times 10^5$ | $1.1 \times 10^8$ | $1.510^8$ | $3.8 \times 10^8$ | $3.8 \times 10^8$ | $5.8 \times 10^7$ | $3.4 \times 10^7$ | N/T |
| S. mutans (35° C.) | $1.6 \times 10^5$ | $1.5 \times 10^8$ | $1.0 \times 10^8$ | $1.2 \times 10^8$ | $1.0 \times 10^8$ | $9.4 \times 10^7$ | $8.0 \times 10^7$ | N/T |
| S. pyogenes (35° C.) | $8.6 \times 10^4$ | $6.2 \times 10^7$ | $2.1 \times 10^8$ | N/T | N/T | $9.4 \times 10^7$ | $8.4 \times 10^7$ | N/T |
| P. aeruginosa (35° C.) | $2.3 \times 10^5$ | $2.1 \times 10^8$ | $2.3 \times 10^6$ | $1.8 \times 10^6$ | $1.8 \times 10^6$ | $1.9 \times 10^6$ | $1.9 \times 10^6$ | $2.6 \times 10^6$ |
| Oral (35° C.) | $7.3 \times 10^3$ | $4.7 \times 10^8$ | $3.9 \times 10^8$ | N/T | N/T | $2.0 \times 10^8$ | $1.3 \times 10^8$ | $3.3 \times 10^8$ |

N/T = Not Tested

II. Factors Influencing MIBC

A. Sialic Acid

Since GMP was so effective at a lower concentration for both S. mutans and A. haemophilus, pure sialic acid (N-acetylneuraminic acid) was tested to see if it alone was the driving force of microbial inhibition. The sialic acid content in GMP is approximately 6.5% (DMV International Nutritionals, 1999). Therefore, a set concentration of 1,000 ppm was applied to three of the oral pathogens (S. mutans, A. haemophilus, and P. aeruginosa). This was a significantly higher than normal amount of sialic acid. Should the results at this high concentration work, further studies at lower sialic acid concentrations would then be tested. Sialic acid, in itself, did not reduce the bacterial growth at this concentration (see Table 5). In the case of P. aeruginosa, sialie acid increased the amount of bacterial growth by one log,. Therefore, GNiIP's and LF's chemical compositions contribute more to the inhibition of bacteria, which the sialic acid alone cannot do.

TABLE 5

Bacteria + Sialic Acid

| Bacteria | Initial | 0 ppm | 1,000 ppm | Log Difference |
|---|---|---|---|---|
| S. mutans | $1.0 \times 10^5$ | $8.9 \times 10^7$ | $5.4 \times 10^7$ | 0 |
| A. haemophilus | $4.8 \times 10^5$ | $3.1 \times 10^8$ | $2.9 \times 10^8$ | 0 |
| P. aeruginosa | $8.7 \times 10^4$ | $9.4 \times 10^8$ | $1.0 \times 10^9$ | +1 |

B. Sodium Bicarbonate at a Low pH (4.36)

This test proved that sodium bicarbonate was not an influencing factor in the reduction of bacterial growth. One ml of the three bacteria tested (S. mutans, A. haemophilus, and P. aeruginosa) were inoculated separately into BHI broth tubes and one ml of sodium bicarbonate, adjusted to a pH of 4.36 by using 0.1N HCl, was also added. Pour plate counts revealed that the low pH slightly effected S. mutans, by causing a one log reduction in the bacteria population, but the other two bacteria were not influenced (see Table 6). In the case of GMP and LF, they are contributing to the reduction of microbial growth. This test proved that acid conditions established from a low pH cannot, by itself, reduce bacteria populations. The oral flora was not tested in this experiment.

TABLE 6

Bacteria + Sodium Bicarbonate (pH 4.36)

| Bacteria | Initial | 0 ppm | 1,000 ppm | Log Difference |
|---|---|---|---|---|
| S. mutans | $1.6 \times 10^5$ | $1.6 \times 10^8$ | $8.4 \times 10^7$ | −1 |
| A. haemophilus | $1.0 \times 10^5$ | $3.5 \times 10^8$ | $1.9 \times 10^8$ | 0 |
| P. aeruginosa | $5.7 \times 10^4$ | $7.0 \times 10^6$ | $6.0 \times 10^6$ | 0 |

III. Identifying the MIBC of Mixtures of LF and GMP

The purpose of this experiment was to combine the MIBC of LF and GUT to assess whether a greater log, reduction in microbial growth was observed. Since the growth of S. mutans and A. haemophilus was reduced by one log at 3,000 ppm LF and one log, at 500 ppm GMP, LF and GMP at these concentrations were tested together using these strains and an oral culture. For these three bacterial cultures (A. haemophiluts, S. mutans and oral flora), the MIBC of both LF and GMT were added. Theoretically, the final effect should have shown at least a two log reduction. Surprisingly, only S. mutans showed a one log reduction. The others showed very little growth reduction (see Table 7).

TABLE 7

Bacteria + LF + GMP Combined

| Bacteria | Initial | 0 ppm | 3,000 LF + 500 GMP | Log Difference |
|---|---|---|---|---|
| A. haemophilus | $1.0 \times 10^5$ | $2.7 \times 10^8$ | $2.5 \times 10^8$ | 0 |
| S. mutans | $1.6 \times 10^6$ | $1.8 \times 10^8$ | $9.3 \times 10^7$ | 1 |
| Oral | $7.1 \times 10^3$ | $4.7 \times 10^8$ | $3.4 \times 10^8$ | 0 |

IV. Varying the LF and GASP Concentrations

Figure 2:
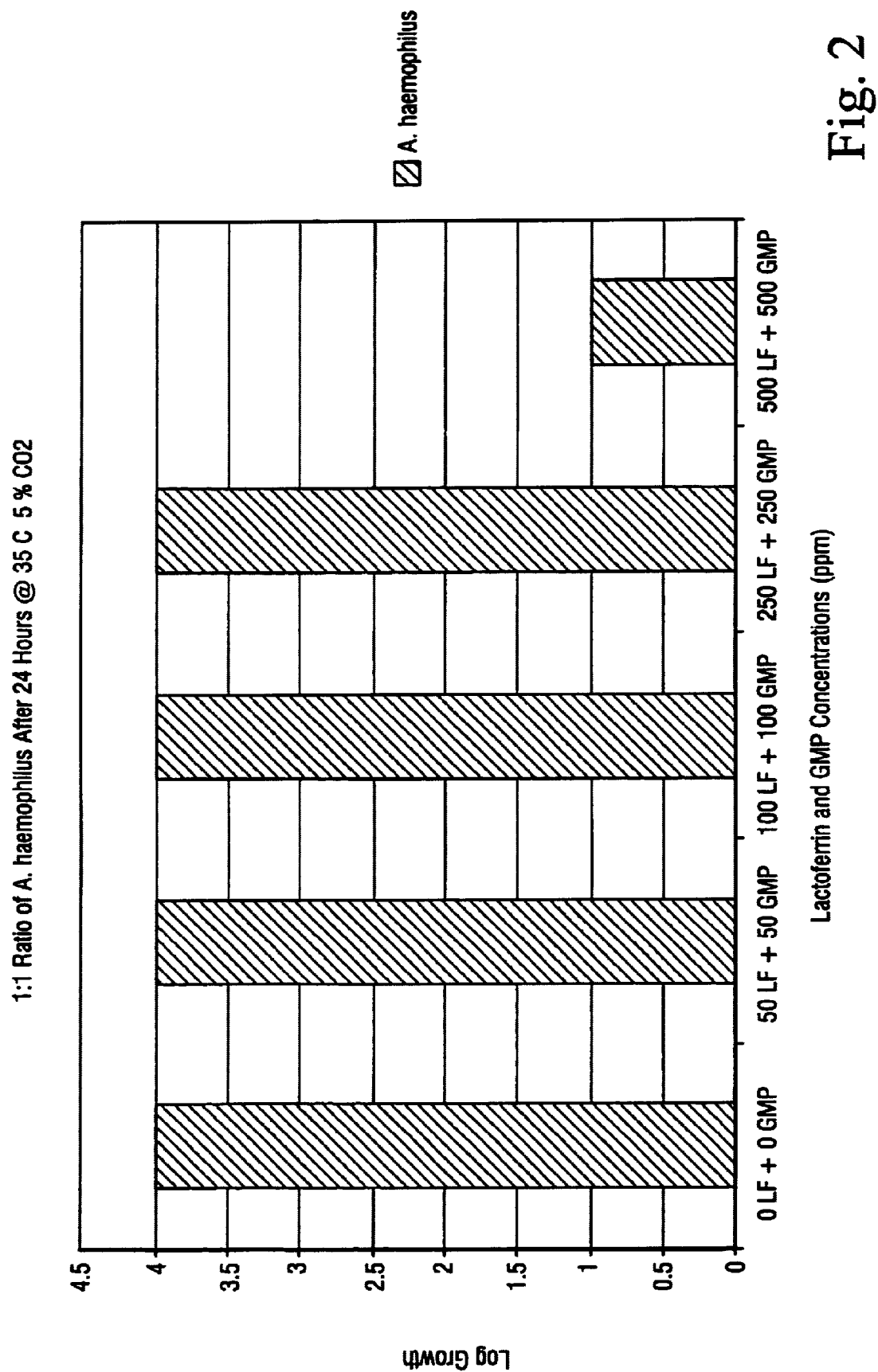
FIG. 2 shows log growth of *A. haemophilus* after 24 hours at 35° C., 5% $CO_2$, in the presence of various 1:1 ratios of LF and GMP.

To test varying concentrations, it was decided to keep the concentration of GMP constant and use different LF concentrations. The lowest successful concentration recorded for S. mutans and A. haemophilus was 500 ppm GMP. Since cost efficiency was an issue, 500 ppm GMP was used as the constant and varying LF concentrations were tested. The varying concentrations of LF were as follows: 0, 25, 50, 75, 100, 200, 250, 400, 500, 750, 1000, 2000 and 3000 ppm. S. mutans showed a one log reduction at the concentration combination of 50 ppm LF+500 ppm GMP. A. haemophilus showed a three log reduction at 500 ppm LF+500 ppm GMP (see FIG. 1). Further testing of A. haemophilus at a 1:1 ratio did not prove to be effective at lower concentrations (see FIG. 2). This test indicated that an exact concentration is required rather than particular ratios.

Testing S. pyogenes and oral bacteria was more difficult because they appeared to be more resistant to the LF and GMP combinations. Using the same combinations as S. mutans and A. haemophilus, they showed no growth reduction.

Figure 3A:
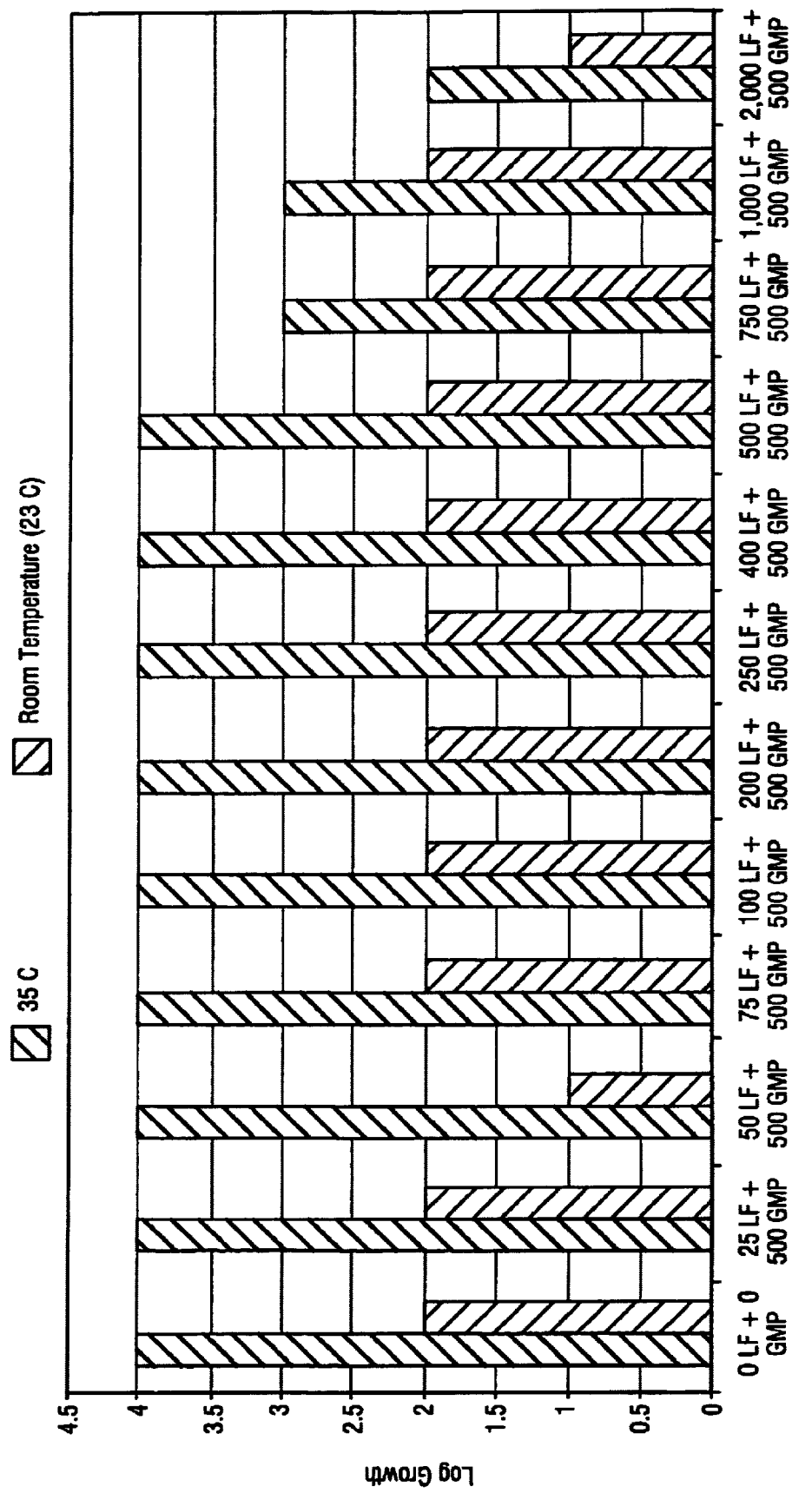
FIGS. 3A and 3B shows log growth of *P. aeruginosa* after 24 hours at 23° C. and 35° C., 5% $CO_2$, FIG. 3A, in the presence of varying concentrations of LF and 500 ppm GMP and, FIG. 3B, in the presence of varying concentrations of GMP and 500 ppm LF.

P. aeruginosa was tested at room temperature (23° C.) and 35° C. with 5% $CO_2$. Since Pseudomonas is an environmental organism, it is a threat at both temperatures. In each setting, the results were different. P. aeruginosa grows abundantly at higher temperatures, but there are combinations of LF and GMP that work for this bacterium within that setting. The combinations that work are: 750 LF+500 GMP, 1,000 LF+500 GMP, and 2,000 LF+500 GMP. At room temperature, the combination concentrations that were effective were: 50 LF+500 GMP and 1,000 LF +500 GMP (see FIG. 3A).

Figure 3B:
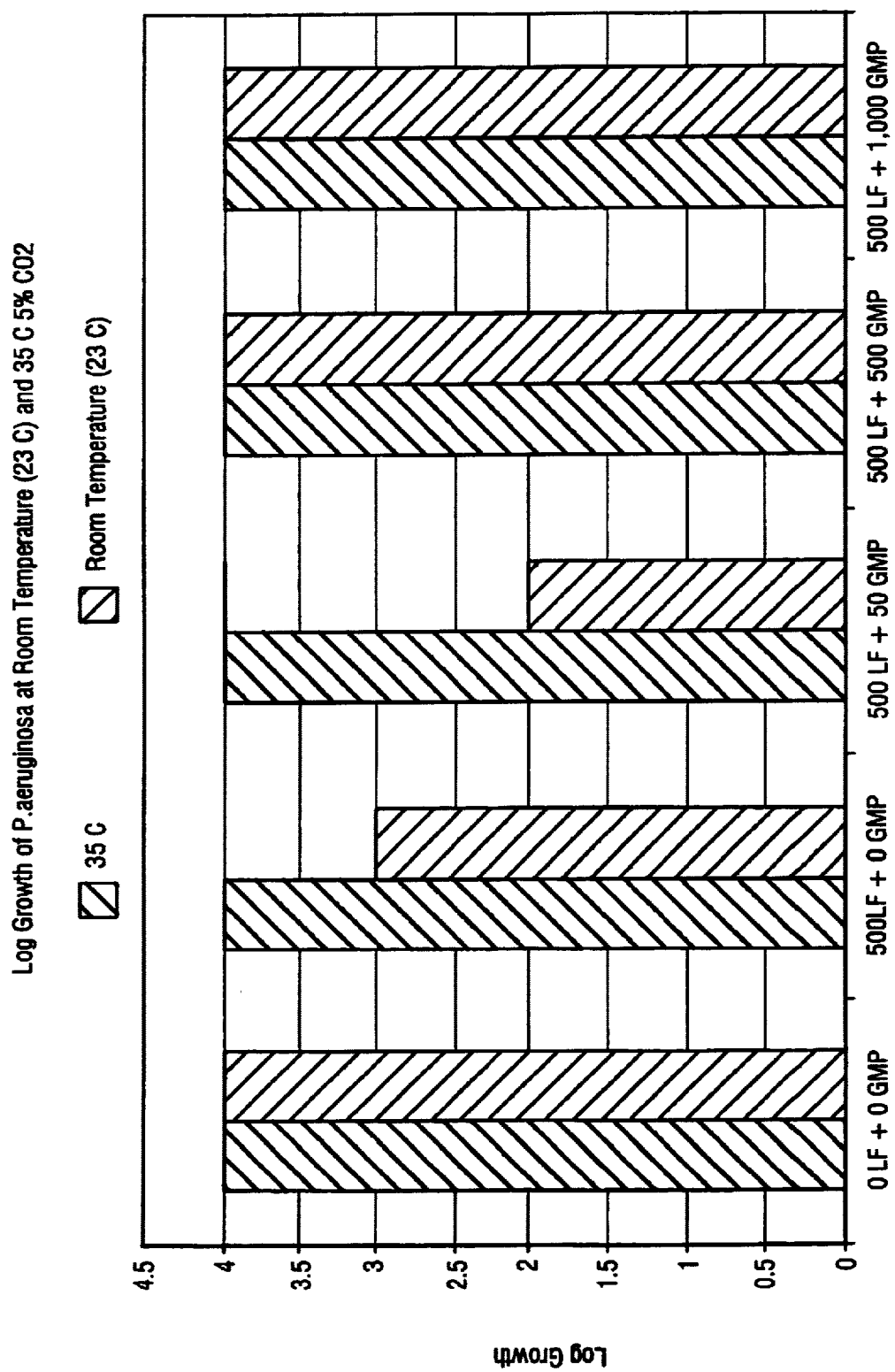
Figure 4:
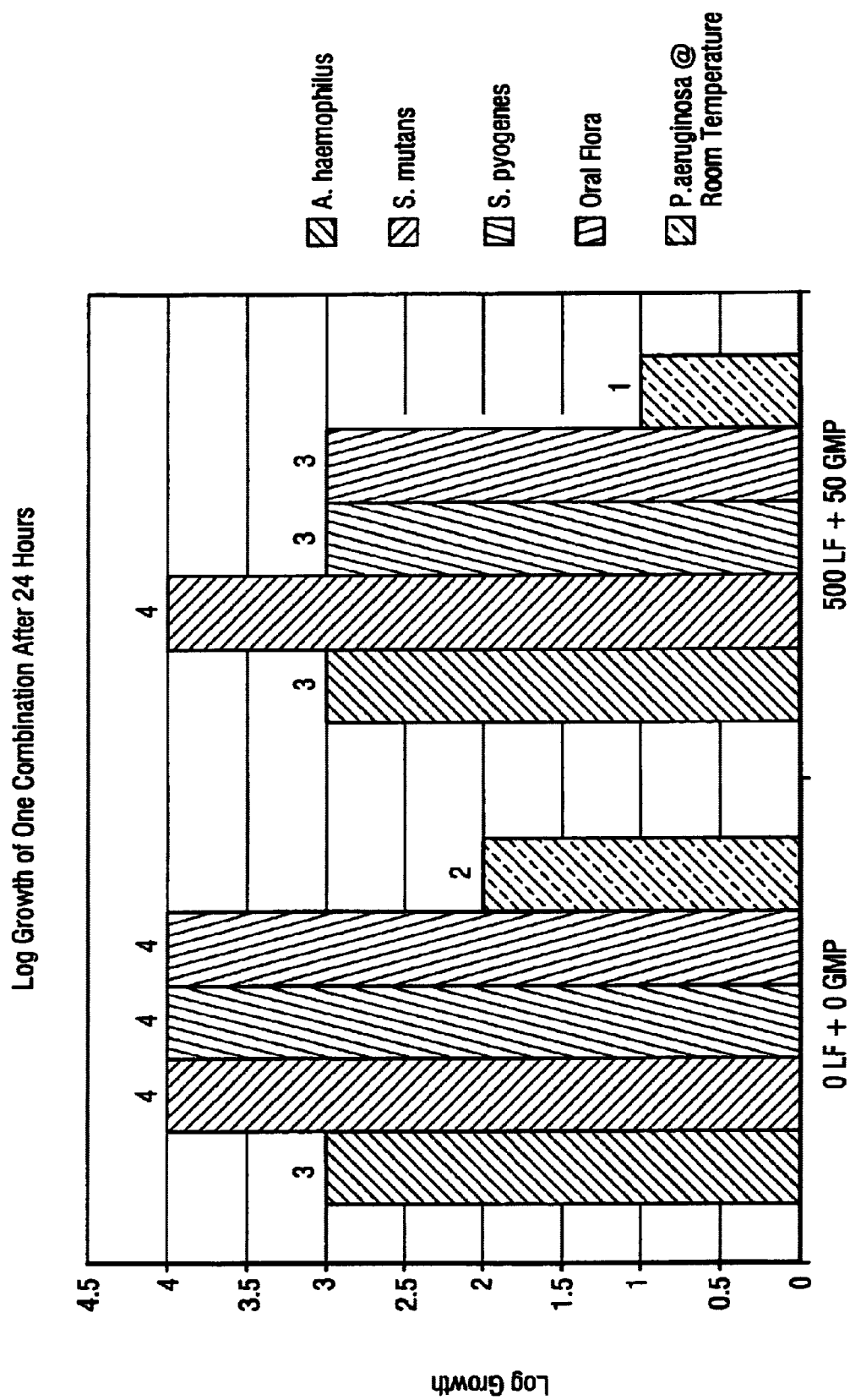
FIG. 4 shows log growth of *A. haemophilus, S. mutans, S. pyrogeus*, and oral flora after 24 hours at 35° C., 5% $CO_2$, and *P. aeruginosa* at room temperature, in the presence of 500 ppm LF and 50 ppm GMP.

A test was also run to determine if varying the GMP concentration while keeping the LF concentration constant would have an effect on P. aeruginosa growth. Testing at both room temperature and 35° C., a two log reduction was observed at room temperature with a combination concentration of 500 LF+50 GMP (see FIG. 3B). This combination was then tested on all four bacteria, with a one log reduction for S. pyogenes, oral flora, and P. aeruginosa being observed (see FIG. 4).

VI. Successful Combinations for all Bacteria Tested

Figure 5:
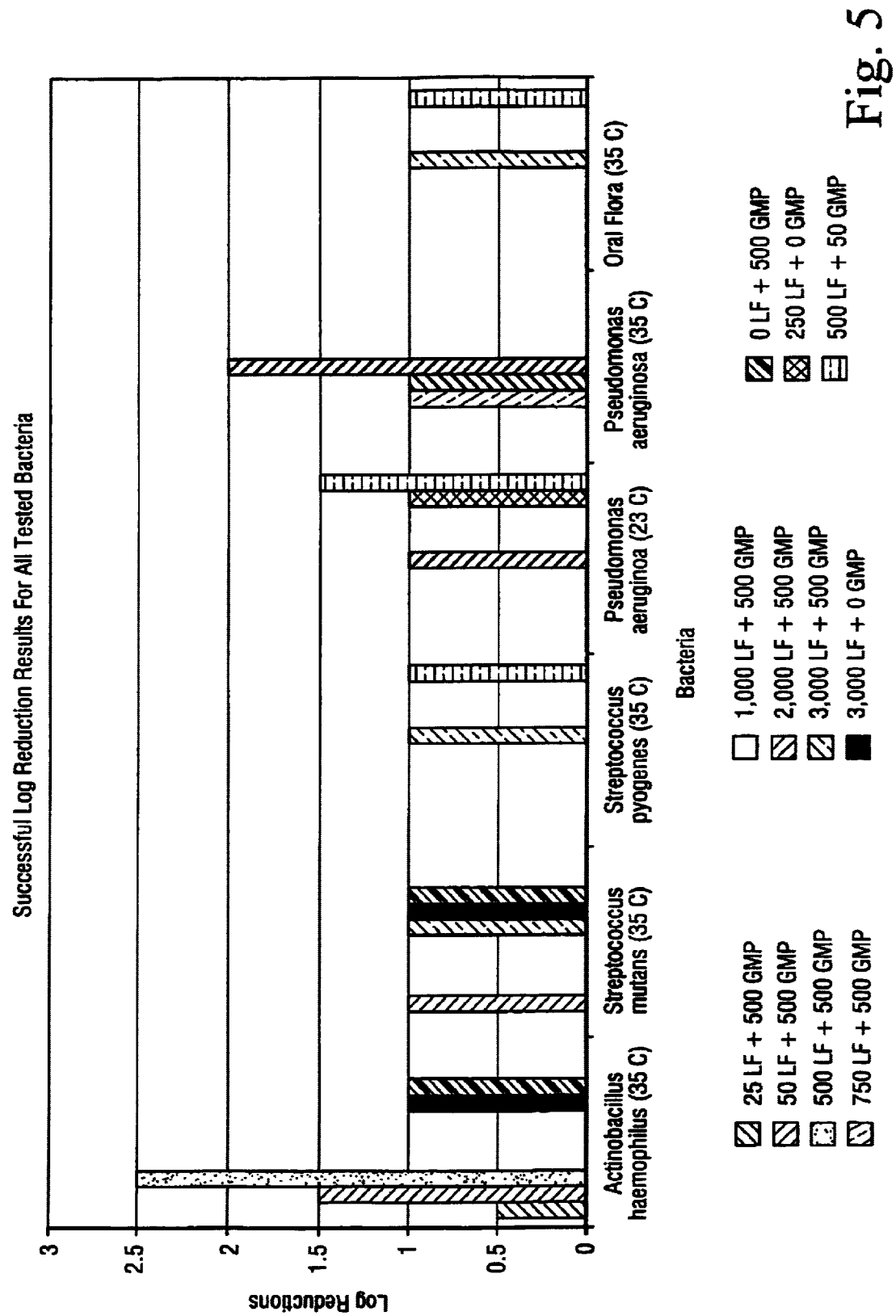
FIG. 5 shows log reduction results for all tested bacteria.

In the final results, there was not one set concentration of LF/GMP, either together or separately, that effectively inhibited microbial growth in all bacteria strains. All bacteria showed a one log reduction in response to at least one of the concentrations tested (see Table 8). The greatest log reductions were found with A. haemophilus and P. aeruginosa at 35° C. with 5% $CO_2$. At a concentration of 500 ppm LF+500 ppm GMP, A. haemophilus dropped 2.5 to 3 logs and at 50 LF+500 GMP it dropped 1.5 logs. Pseudomonas at 35° C. dropped 2 logs with 2,000 LF+500 GMP. At room temperature (23° C.), Pseudomonas dropped 1 to 1.5 logs with the concentration 500 LF+50 GMP (see Table 8 and FIG. 5).

All documents cited above are hereby incorporated in their entirety by reference.

One skilled in the art will appreciate from a reading of this disclosure that various chances in form and detail can be made without departing from the true scope of the invention.

What is claimed is:

1. A method of treating or reducing the incidence of a disease or disorder of the oral cavity of a patient comprising contacting said oral cavity with an effective amount of a combination of lactoferrin (LF) and glycomacropeptide (GMP) that exerts an antimicrobial effect on microorganisms present in said oral cavity, wherein said antimicrobial effect is an anti-Actinobacillus haemophllus effect, an anti-Pseudomonas aeruginosa effect and an anti-Streptococcus pyogenes effect.

2. The method according to claim 1 wherein said disease is dental plaque.

3. The method according to claim 1 wherein said disease is gingivitis.

4. The method according to claim 1 wherein said combination is 500 ppm LF and 500 ppm GMP.

5. The method according to claim 1 wherein said combination of LF and GMP is 500 ppm LF and 50 ppm GMP.

6. A method of exerting an antimicrobial effect at a site in the oral cavity of a patient comprising applying to said site a composition comprising LF and GMP in admixture in an amount such that said composition exerts said antimicrobial effect, wherein said antimicrobial effect is an anti-Actinobacillus haemophilus effect, an anti-Pseudomonas

TABLE 8

Total Log Reduction of Mixture Combinations

| Lactoferrin/<br>GMP | 25/500 | 50/500 | 500/500 | 750/500 | 1,000/<br>500 | 2,000/<br>500 | 3,000/<br>500 | 3,000/0 | 0/500 | 250/0 | 500/50 |
|---|---|---|---|---|---|---|---|---|---|---|---|
| Actinobacillus haemophilus (35° C.) | 0.5 | 1.5 | 2.5 | 0 | 0 | 0 | 0 | 1 | 1 | 0 | 0 |
| Streptococcus mutans (35° C.) | 0 | 1 | 0 | 0 | 0 | 0 | 1 | 1 | 1 | 0 | 0 |
| Streptococcus pyogenes (35° C.) | 0 | 0 | 0 | 0 | 0 | 0 | 1 | 0 | 0 | 0 | 1 |
| Pseudomonas aeruginosa (23° C.) | 0 | 0 | 0 | 0 | 0 | 1 | 0 | 0 | 0 | 1 | 1 |
| Pseudomonas aeruginosa (35° C.) | 0 | 0 | 0 | 1 | 1 | 2 | 0 | 0 | 0 | 0 | 0 |
| Oral Flora (35° C.) | 0 | 0 | 0 | 0 | 0 | 0 | 1 | 0 | 0 | 0 | 1 |

This study confirmed previous work that LF and GMP have some antimicrobial capabilities. While they are not total inhibitors, they do show effectiveness in reducing the ability of certain organisms to proliferate. Surprisingly, a very good synergistic effect at certain concentration combinations was observed. For example, the 500/500 ppm LF/GMP combination was highly effective against A. haemophilus.

aeruginosa effect and an anti-Streptococcus pyogenes effect.

7. The method according to claim 6 wherein said composition comprises 500 ppm LF and 500 ppm GMP.

8. The method according to claim 6 wherein said composition comprises 500 ppm LF and 50 ppm GMP.

* * * * *